United States Patent [19]

Thibault

[11] 4,209,300
[45] Jun. 24, 1980

[54] HEMOGLOBIN-OXYGEN EQUILIBRIUM CURVE ANALYZER

[75] Inventor: Lawrence E. Thibault, Rockville, Md.

[73] Assignee: The United States of America as represented by the Department of Health, Education and Welfare, Washington, D.C.

[21] Appl. No.: 945,130

[22] Filed: Sep. 25, 1978

[51] Int. Cl.² .................... G01N 33/16; G01N 27/30; G01N 27/40

[52] U.S. Cl. .................................. 23/230 B; 73/1 G; 73/19; 204/1 T; 204/195 B; 204/195 P; 324/71 R; 422/68

[58] Field of Search .................. 23/230 B; 422/79, 80, 422/81, 88, 98, 68; 204/195 B, 195 P

[56] References Cited

U.S. PATENT DOCUMENTS

| Re. 29,769 | 9/1978 | Kiesow | 23/230 B |
|---|---|---|---|
| 3,701,716 | 10/1972 | Deuringer | 195/127 |
| 3,779,708 | 12/1973 | Runck | 23/230 B |
| 3,854,878 | 12/1974 | Kiesow | 23/230 B |
| 3,868,223 | 2/1975 | Robock | 23/230 B X |
| 3,904,209 | 9/1975 | Kiesow | 356/246 |
| 3,997,419 | 12/1976 | Scott | 204/195 P |
| 4,013,417 | 3/1977 | Raffaele | 23/230 B |
| 4,014,649 | 3/1977 | Kiesow | 23/230 B |
| 4,066,361 | 1/1978 | Achter | 356/41 |
| 4,092,233 | 5/1978 | Clemens | 204/195 B |
| 4,109,505 | 8/1978 | Clark | 204/195 B |
| 4,120,658 | 10/1978 | Bruttig | 23/230 B |

OTHER PUBLICATIONS

Abstract, "An Instrument for the Automated Determination of the Hemoglobin–Oxygen Equilibrium Curve," by L. Thibault and R. Kusnetz, National Institutes of Health, Aug. 24, 1977.

Abstract, "An Instrument to Determine the Hemoglobin–Oxygen Equilibrium Curve Based on an Analytical Model for the Transport of Oxygen Across a Semi--Permeable Membrane," by L. E. Thibault, R. Kusnetz, R. M. Winslow & R. L. Berger, National Institutes of Health, May 15, 1978.

Primary Examiner—Sidney Marantz
Attorney, Agent, or Firm—Browdy and Neimark

[57] ABSTRACT

A system for obtaining a hemoglobin-oxygen equilibrium curve for a sample of concentrated hemoglobin solution or whole blood. Gaseous oxygen and/or nitrogen is used to oxygenate or deoxygenate the sample. The exchange takes place across a gas-receiving cup-shaped semipermeable membrane in a temperature-controlled chamber containing the sample, in an annular space defined between the cup-shaped gas-receiving membrane and the chamber wall. The rate of oxygen transport into and out of the sample is continuously calculated by means of a microcomputer. Simultaneously the solution $pO_2$ is measured by means of a Clark electrode exposed to the sample. From the oxygen transport rate calculation and the $pO_2$ measurement, the percent $O_2$ saturation is calculated and is plotted against the change in $pO_2$. Oxygen can be exchanged bidirectionally with the sample across the semipermeable membrane, which is positioned concentrically in a cylindrical sample cavity. The sample solution is maintained well-stirred by a magnetic stirrer provided in the cavity.

15 Claims, 3 Drawing Figures

HEMOGLOBIN-OXYGEN EQUILIBRIUM CURVE ANALYZER

FIELD OF THE INVENTION

This invention relates to systems for obtaining hemoglobin-oxygen equilibrium curves, and more particularly to a method and means for obtaining such curves based on the computation of the rate of oxygen transport into and out of a sample via a semipermeable membrane.

BACKGROUND OF THE INVENTION

Various systems have been proposed for obtaining or deriving oxygen association rate curves for a blood sample or a hemoglobin solution. These systems fall into two general categories, namely, (1) systems of the optical type, measuring absorbance of a monochromatic beam as a function of oxygenation of the sample, or (2) systems electrically measuring transport of oxygen through a gas-permeable membrane without relying on optical measurements. Typical prior art systems of the optical type employ dual-wavelength spectrometry, involving fairly complex and expensive optical apparatus.

In another typical prior art system (Winslow, R. M. etal, Journal of Biological Chemistry, Vol. 252, No. 7, April 1977, pp. 2331-2337) the source of oxygen is hydrogen peroxide. The $H_2O_2$ is pumped into a whole blood sample and is reduced in the presence of catalase to form $O_2$ and water. An advantage of the $H_2O_2$ method is that the percent saturation is more precisely determined than by conventional dual-wavelength spectrometry. However, $H_2O_2$ cannot be used with hemoglobin solutions because it is too violent an oxidizing agent. Further, since $H_2O_2$ is being added to the whole blood sample, the system must be capable of changing volume with no total pressure change, i.e., must be open to the atomsphere. This causes problems with red blood cell settling and/or $O_2$ diffusion from the atmosphere. Finally, the prior system does not permit one to investigate the hemoglobin-oxygen dissociation curve, i.e., the system cannot be run in reverse.

SUMMARY OF THE INVENTION

The system of the present invention utilizes gaseous oxygen and/or nitrogen to oxygenate or deoxygenate concentrated hemoglobin solution or whole blood. Exchange takes place across a semipermeable membrane. The rate of oxygen transport into or out of the sample solution is continuously calculated by using a microcomputer. From the computations and the simultaneous measurement of the solution $pO_2$ the percent saturation is then calculated. The system is completely closed, i.e., has constant volume.

Accordingly, a main object of the present invention is to provide a novel and improved system for obtaining hemoglobin-oxygen equilibrium curves which overcomes the deficiencies and disadvantages of prior systems employed for this purpose.

A further object of the invention is to provide an improved method and apparatus for obtaining hemoglobin-oxygen equilibrium curves which can be employed with either whole blood samples or with concentrated hemoglobin solutions.

A still further object of the invention is to provide an improved apparatus for obtaining hemoglobin-oxygen equilibrium curves which is closed from the atmosphere and employs a constant-volume working chamber.

A still further object of the invention is to provide an improved method for obtaining hemoglobin-oxygen equilibrium curves which does not require the optical determination of percent saturation.

A still further object of the invention is to provide an improved system for obtaining hemoglobin-oxygen equilibrium curves which can be run in reverse, permitting the study of oxygen dissociation curves and eliminating the need for a tonometer.

A still further object of the invention is to provide an improved apparatus for obtaining hemoglobin-oxygen equilibrium curves which can be employed to measure the hemoglobin-oxyhemoglobin curve during both oxygenation and deoxygenation and which employs a semipermeable membrane for oxygen exchange with a sample (concentrated hemoglobin solution or whole blood), simultaneously monitoring the partial pressure of oxygen in solution and determining the percent saturation of the hemoglobin, the exchange of oxygen taking place across the semipermeable membrane in a very physiological manner, the $pO_2$ being constantly monitored and the percent saturation being calculated from an analytical model of the transport of oxygen across the membrane.

BRIEF DESCRIPTION OF THE DRAWINGS

Further objects and advantages of the invention will become apparent from the following description and claims, and from the accompanying drawings, wherein:

DESCRIPTION OF A PREFERRED EMBODIMENT

Figure 1:
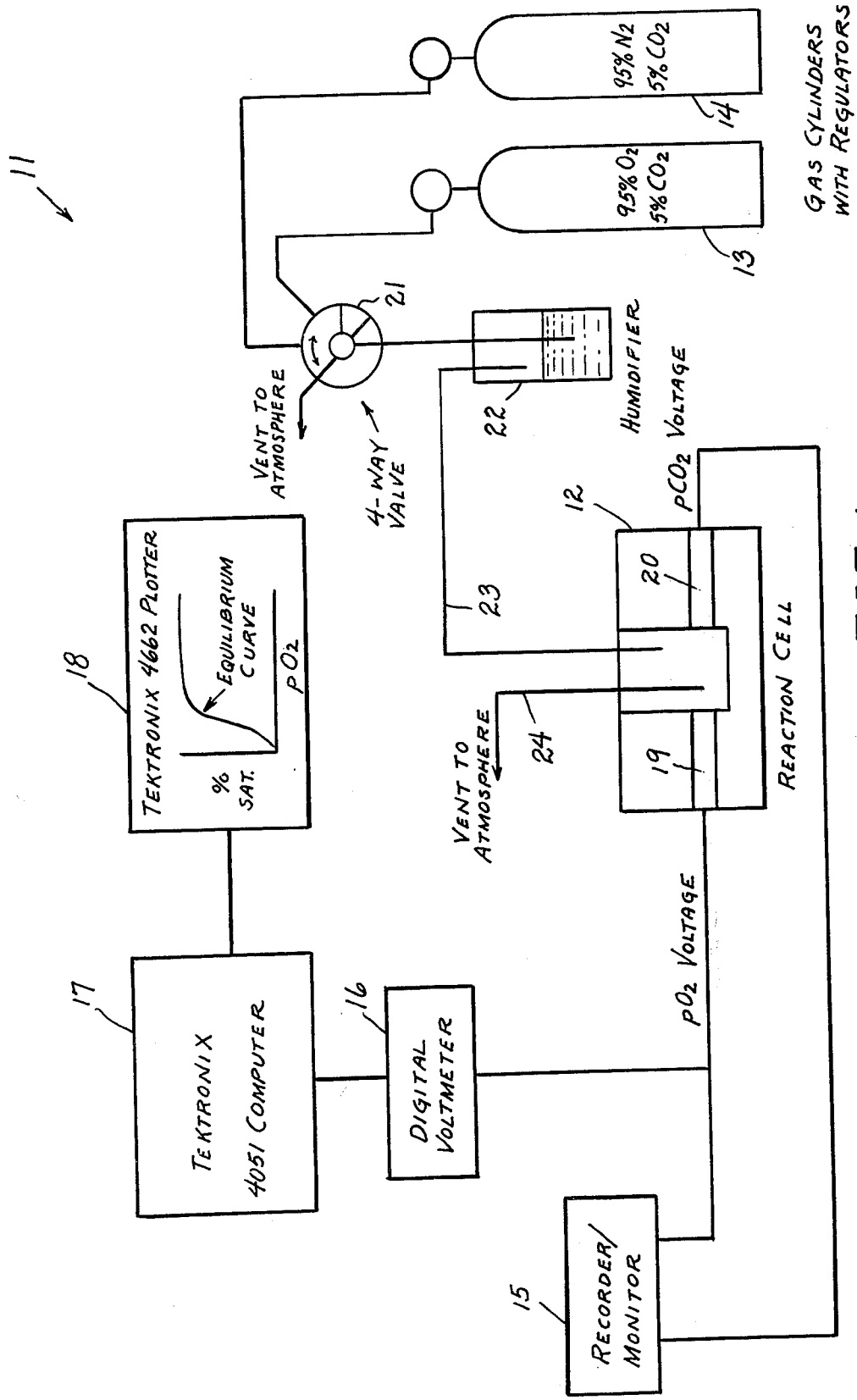
FIG. 1 is a block diagram showing an improved system for obtaining hemoglobin-oxygen equilibrium curves in accordance with the present invention.

Referring to the drawings, FIG. 1 shows diagrammatically a typical apparatus, designated generally at 11, according to the present invention. The apparatus 11 comprises a reaction cell 12, gas supply cylinders 13, 14, a conventional recorder/monitor 15, a digital voltmeter 16, a conventional microcomputer 17, and a conventional plotter or display device 18. The reaction cell 12 includes a conventional Clark-type electrical oxygen electrode 19 and a conventional electrical $CO_2$ electrode 20 interfaced to the sample solution, as will be presently described. The gas supply cylinders 13, 14 are connected selectively to the reaction cell 12 through a conventioanl 4-way selector valve 21 and a humidifier 22. Humidified gas is furnished to the reaction cell 12 via a conduit 23 and flows from the cell 12 to atmosphere via a vent conduit 24.

Figure 2:
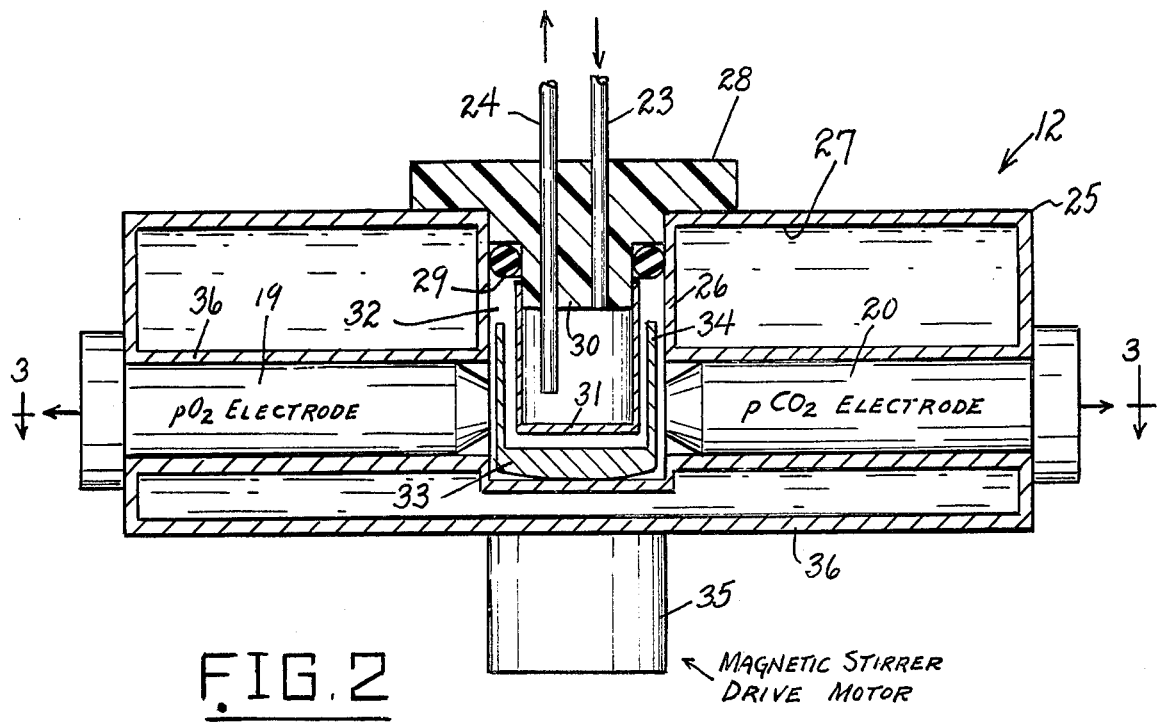
FIG. 2 is a longitudinal vertical cross-sectional view taken through the reaction cell employed in the system of FIG. 1.
Figure 3:
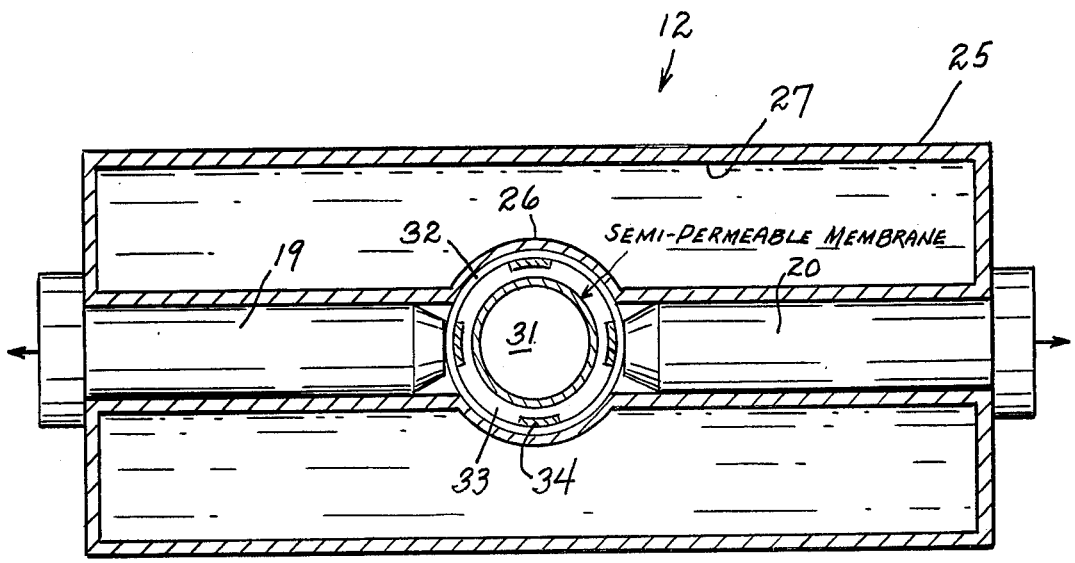
FIG. 3 is a horizontal cross-sectional view taken substantially on the line 3—3 of FIG. 2.

Referring to FIGS. 2 and 3, the reaction cell 12 comprises a housing 25 formed with a vertical cylindrical working chamber 26 surrounded by a water jacket 27 filled with water maintained at a substantially constant temperature by suitable conventional means, not shown. A flanged cover plug 28 of suitable resilient yieldable material, such as KEL-F, or the like, is tightly engageable in the top end of chamber 26 and is provided with an O-ring 29 sealingly engageable between the wall of chamber 26 and a reduced depending central boss 30 integrally formed on plug 28. A cylindrical, thinwalled, molded silicone rubber membrane, which is cup-shaped, is secured on and depends coaxially from the lower end portion of boss 30, defining an annular sample space 32 between the cup-shaped membrane 31 and the cylindrical wall of chamber 26.

As shown in FIG. 2, the gas supply conduit 23 extends vertically and sealingly through the plug 28 and opens into the top portion of cup 31. The vent conduit 24 extends sealingly through the plug 28 and connects the lower portion of cup 31 to the atmosphere.

A freely rotatable magnetic stirrer body member 33 is provided in the bottom of chamber 26, said body member having a plurality of upstanding vertical stirrer arms 34 extending in the annular space 32. The body member 33 is driven by magnetic coupling in a conventional manner by a magnetic stirrer drive motor 35 secured to the bottom wall 36 of housing 25.

The $pO_2$ electrode 19 is mounted in a horizontal supporting casing 36 formed in housing 25, with its sensing end exposed to the annular sample space 32. The $pCO_2$ electrode 20 is similarly mounted, with its sensing end likewise exposed to space 32, as shown in FIGS. 2 and 3.

As will be apparent from FIG. 2, the KEL-F insert plug 28 ensures that the thin-walled molded silicone rubber membrane 31 is positioned concentrically in the cylindrical sample chamber 26, thereby forming the extended annular sample space 32 for the fluid under study. This fluid is well-stirred by the magnetically coupled stirrer arms 34 rotating in the annular region and providing effective mixing of the gas from cup 31 with the fluid in space 32. In a typical design, the volume of sample space 32 was approximately 500 microliters.

In a typical mode of operation, a suitable amount of sample (concentrated hemoglobin solution or whole blood) is introduced into the space in the chamber 26 and the plug 28 with the attached cup-shaped semipermeable membrane 31 is placed in operating position, as shown in FIG. 2, forcing the sample liquid to be distributed in the annular space 32. By means of valve 21, nitrogen from tank 4, containing carbon dioxide to insure that physiological levels of $CO_2$ are maintained, is introduced into the hollow cavity defined by cup-shaped membrane 31. The sample solution then completely desaturates to zero oxygen. When this point is reached, as observed on the recorder/monitor 15, the 4-way valve 21 is switched so that oxygen containing carbon dioxide, from tank 13, is introduced into cup 31. The $PO_2$ (as detected by electrode 19) is continuously recorded and the data are stored in the microcomputer 17.

The exchange rate $\dot{M}_{O2}$ of oxygen across a membrane into a well-stirred solution is governed by the diffusion equation, which is of the form $$\dot{M}_{O2} = v\frac{dp}{dt} = \bar{P}A(p^* - p) \tag{1}$$

where p=p(t), which is a time function, and the solution of which is given by $$p(t) = p^*(1 - e^{\frac{-\bar{P}A}{VVK_b}t}) \tag{2}$$

where v, $\bar{P}$, A, $p^*$, V, and $V_{kb}$ are constants for a given apparatus. However, the solubility of the membrane itself must be taken into account, and therefore the solution is more properly given as $$p(t) = p^*(1 - e^{\frac{-\bar{P}A}{V}t} - e^{\frac{-\bar{P}_1A_1}{V_1}t}) \tag{3}$$

wherein A and $A_1$ represent the respective areas of the sample solution and membrane, v and $v_1$ respectively represent the volumes of the sample solution and membrane, and $\bar{P}$ and $\bar{P}_1$ represent the respective permeabilities of the sample solution and membrane.

The percent of hemoglobin which is saturated with oxygen is related to the difference in the mass transport of oxygen across the semipermeable membrane and the partial pressure of oxygen in solution in the sample.

If there was no chemical binding of oxygen by the sample solution there would be no difference between the mass transport of oxygen across the membrane and the change in partial pressure of the oxygen in the sample solution. They would be related simply by the solubility of oxygen in the sample solution and the solubility of oxygen in the silicone rubber membrane.

The method of computing the ordinates of the hemoglobin-oxygen equilibrium curve is given therefore as follows:

$$\% \text{ Saturation} = \dot{M}_{O2} - KP_B \tag{4}$$

where $P_B$ represents the $PO_2$ in the sample solution and K is a constant.

Therefore $$\% \text{ Saturation} = P^*(1 - e^{-at} - e^{-bt}) - KP_B \tag{5}$$

This equation is programmed in the software for the Tektronix 4051 computer. Scaling for 0–100% saturation is based on the assumption that the sample solution is fully saturated at a partial pressure of 150 mm Hg. This value is arbitrary but has been shown to be experimentally valid. The constants $p^*$, a, b, and K are determined experimentally by saturating a sample of serum with oxygen in the apparatus of the present invention.

The difference between the total oxygen transferred and the oxygen in solution, as measured by the $pO_2$ electrode 19, is that which is bound to hemoglobin.

These calculations are performed by the Tektronix 4051 computer 17, and the data may be stored on cassette tape or presented on the Tektronix 4662 digital plotter 18. The oxygen electrode analog voltage from electrode 19, which is proportional to the partial pressure of oxygen in the sample solution is digitized by the digital voltmeter 16, which may be similar to the Data Precision 3400 Digital Multimeter.

The values of the constants used in the solution of the equation for the transfer of oxygen into the sample solution are determined experimentally by exchanging oxygen with samples of saline and serum.

The equilibrium curve shown by the plotter 18 shows the percent saturation of the sample during oxygenation as a function of $pO_2$.

The system can then be run in reverse by switching the 4-way valve 21 and introducing nitrogen containing carbon dioxide into the sample. The result shown on the plotter 18 will be the desaturation curve for the sample solution.

As will be seen from FIG. 2, during operation, either for obtaining the oxygen association curve or the oxygen dissociation curve, the interior of the cup-shaped semipermeable membrane 31 is continuously exposed to a constant flow of gaseous reagent, entering the upper portion of the cup-shaped membrane via the inlet conduit 23 and leaving the lower portion of the cup-shaped membrane via the vent conduit 24.

While a specific embodiment of an improved hemoglobin-oxygen equilibrium curve analyzing system has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment. For example, certain pieces of equipment are mentioned above with regard to the description of a preferred embodiment, but it will be understood that other functionally equivalent pieces of equipment may be used instead; similarly, certain materials, such as KEL-F are mentioned, but it will be understood that elements may be formed of other materials as well.

Reference is made to an Abstract relative to the invention, and entitled "An Instrument for the Automated Determination of the Hemoglobin-Oxygen Equilibrium Curve"(unpublished), which is incorporated by reference. Also incorporated by reference is a copy of another Abstract relating to the present invention and entitled "An Instrument to Determine the Hemoglobin-Oxygen Equilibrium Curve Based on an Analytical Model for the Transport of Oxygen Across a Semipermeable Membrane" ; 1978 *Advances in Bioengineering,* December 10–15, 1978, pages 107–108.

What is claimed is:

1. An apparatus for obtaining a hemoglobin-oxygen equilibrium curve for a sample, comprising housing means including a chamber adapted to receive a quantity of said sample, a cup-shaped semipermeable membrane mounted in said chamber and defining externally thereof a substantially annular sample-receiving space within the chamber, means to supply a gaseous reagent to the interior of said cup-shaped membrane, means to compute the rate of gas transport through the membrane into a sample contained in said annular space, electrode means exposed to said annular space to measure the solution partial pressure of the transported gas in the sample, and means to plot the percent gas saturation in the sample against the changes in said partial pressure.

2. The curve-obtaining apparatus of claim 1, and rotary stirrer means in said annular space.

3. The curve-obtaining apparatus of claim 2, and wherein said stirrer means comprises a rotary magnetic body member with a plurality of upstanding stirrer arms extending into said annular space.

4. The curve-obtaining apparatus of claim 1, and wherein said housing means includes a temperature-controlling water jacket surrounding said chamber.

5. The curve-obtaining apparatus of claim 1, and wherein said chamber is provided with removable top cover means.

6. The curve-obtaining apparatus of claim 5, and wherein said top cover means has a depending boss element, and wherein said cup-shaped membrane is secured to and depends from said boss element.

7. The curve-obtaining apparatus of claim 6, and wherein the means to supply the gaseous reagent includes conduit means extending through said depending boss element.

8. The curve-obtaining apparatus of claim 1, and wherein the means to supply the gaseous reagent comprises at least two containers of different gases, and selector valve means connected between said containers and said cup-shaped semipermeable membrane for selecting the gas to be supplied to the cup-shaped membrane.

9. The curve-obtaining apparatus of claim 1, and vent conduit means connected to the cup-shaped membrane to allow continuous flow-through of gas admitted into the cup-shaped membrane.

10. The curve-obtaining apparatus of claim 1, and wherein said electrode means comprises an oxygen-sensing Clark electrode.

11. The curve-obtaining apparatus of claim 1, and wherein the means to supply the gaseous reagent comprises two containers of different gases, and selector valve means connected between said containers and said cup-shaped semipermeable membrane for selecting the gas to be supplied to the cup-shaped membrane, and wherein said electrode means comprises respective gas-sensing electrodes exposed to said annular space for sensing the different gases.

12. The curve-obtaining apparatus of claim 11, and wherein said chamber is provided with removable top cover means including a depending boss element, wherein said cup-shaped semipermeable membrane is secured on and depends from said boss element, and wherein said gaseous reagent supply means includes gas conduit means extending through said boss element, said selector valve means being connected between said gas conduit means and said two containers.

13. A method for obtaining a hemoglobin-oxygen equilibrium curve for a sample comprising enclosing the sample in a space with a semipermeable membrane on one side, supplying gas to the area of the membrane opposite to the sample for diffusion to the sample, directly measuring the partial pressure of the gaseous oxygen in the sample, determining the rate of oxygen transport into the sample by continuous solution of the diffusion equation, continuously calculating the percent of oxygen saturation, and plotting the percent of oxygen saturation against the changes in partial pressure of the oxygen in the sample.

14. The method of claim 13, and wherein the gas supplied is mainly oxygen.

15. The method of claim 14, and wherein the gas supplied contains a relatively small percentage of carbon dioxide.

* * * * *